(12) United States Patent
Ma et al.

(10) Patent No.: US 11,938,209 B2
(45) Date of Patent: *Mar. 26, 2024

(54) ORAL CARE COMPOSITIONS

(71) Applicant: Firmenich SA, Satigny (CH)

(72) Inventors: Emma Qiu-Min Ma, Shanghai (CN); Wolfgang Fieber, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,035

(22) Filed: Jul. 6, 2022

(65) Prior Publication Data

US 2022/0331214 A1  Oct. 20, 2022

Related U.S. Application Data

(63) Continuation of application No. 16/639,190, filed as application No. PCT/EP2018/085463 on Dec. 18, 2018, now Pat. No. 11,389,383.

(51) Int. Cl.
| | |
|---|---|
| *A61K 8/37* | (2006.01) |
| *A61K 8/34* | (2006.01) |
| *A61K 8/60* | (2006.01) |
| *A61K 8/86* | (2006.01) |
| *A61Q 11/00* | (2006.01) |

(52) U.S. Cl.
CPC .................. *A61K 8/37* (2013.01); *A61K 8/34* (2013.01); *A61K 8/345* (2013.01); *A61K 8/604* (2013.01); *A61K 8/86* (2013.01); *A61Q 11/00* (2013.01)

(58) Field of Classification Search
CPC ......... A61K 31/28; A61K 33/38; A61Q 11/00
USPC .......................................... 424/49, 401, 618
See application file for complete search history.

(56) References Cited

U.S. PATENT DOCUMENTS

| | | |
|---|---|---|
| 4,976,954 A | 12/1990 | Kleber et al. |
| 2006/0051430 A1* | 3/2006 | Arata ..................... A61Q 11/00 514/495 |
| 2012/0114705 A1 | 5/2012 | Zerbe et al. |
| 2012/0244097 A1 | 9/2012 | Lu et al. |
| 2015/0328092 A1 | 11/2015 | Fei et al. |
| 2016/0374352 A1* | 12/2016 | Modak ................. A61K 36/898 424/54 |
| 2021/0196621 A1* | 7/2021 | Modak ................... A61K 31/05 |

FOREIGN PATENT DOCUMENTS

| | | |
|---|---|---|
| CN | 1399542 A | 2/2003 |
| CN | 102639097 A | 8/2012 |
| CN | 104135996 A | 11/2014 |
| WO | 01/22942 A1 | 9/2000 |
| WO | 2013133096 A1 | 9/2013 |

OTHER PUBLICATIONS

International Search Report and Written Opinion of International Application No. PCT/EP2018/085463 dated May 22, 2019; 28 pages.
BASF SE, "Care Chemicals & Formulators, Technical Information Pluracare L/F Grades Poloxamer", Jan. 2008, (XP055565537), URL: http://www.rumapel.com.ar/cosmetica_miscelaneos/ficha_tecnica/Pluracare%20L-%20F%20Grades.pdf.

\* cited by examiner

*Primary Examiner* — Walter E Webb

(57) ABSTRACT

The various aspects presented herein relate to the cooling and flavor boosting compositions, and their use thereof.

20 Claims, No Drawings

ORAL CARE COMPOSITIONS

CROSS REFERENCE TO RELATED APPLICATIONS

The present application is a continuation of U.S. application Ser. No. 16/639,190, filed Feb. 14, 2020, which is a U.S. national phase entry under 35 U.S.C. § 371 of International Application No. PCT/EP2018/085463, filed on Dec. 18, 2018, which claims priority to International Patent Application Serial No. PCT/CN2017/117398, filed on Dec. 20, 2017. The entire contents of these applications are explicitly incorporated herein by this reference.

FIELD OF THE INVENTION

The various aspects presented herein relate to non-alcoholic or slightly-alcoholic oral care compositions, and their use thereof.

BACKGROUND

Oral care preparations, such as, for example, mouthwashes or mouth rinses are developed to clean and refresh the oral cavity or oral surface by inhibiting or killing the microorganisms that cause malodor, dental caries, tooth decay, gum diseases, gingivitis, and periodontal disorders. The effectiveness of an oral care composition may be based on its ability to deliver the active ingredient(s) contained therein, to kill the targeted microorganisms.

Conventional oral care compositions typically contain relatively high levels of $C_2$-$C_4$ monohydric alcohol content, ranging from, for example, 10% to about 30% v/v of ethyl alcohol. The $C_2$-$C_4$ monohydric alcohol may be employed as a disinfectant or solvent for the added excipients such as astringents, fluorides, colors, flavors, and the like. Further, the higher quantity of $C_2$-$C_4$ monohydric alcohol is usually employed to provide a disinfection role since lower amounts are adequate to dissolve the various ingredients of the oral care composition into solution. The $C_2$-$C_4$ monohydric alcohol may also offer a preservative function for the oral care composition during storage, and may enhance the organoleptic or aesthetic properties of an essential oil within the oral care composition.

The use of $C_2$-$C_4$ monohydric alcohols may be problematic from an overall health perspective in part, due to several reasons, including, but not limited to: (i) the contraindication of $C_2$-$C_4$ monohydric alcohol for health and safety related reasons; (ii) abuse of alcohol-containing oral care compositions; (iii) irritation of the protective layers of the mouth and throat; or (iv) dry mouth.

However, reducing the amount of $C_2$-$C_4$ monohydric alcohol in oral care compositions is problematic. Lowering the $C_2$-$C_4$ monohydric alcohol content results in decreased solubility of active ingredients and thereby lesser antimicrobial efficacy of the oral care composition with regard to bad breath, plaque gum disease and the like. Moreover, the use of surfactants to solubilize active ingredients in alcohol-free oral care compositions may also reduce the antimicrobial efficacy of the composition and may cause unpleasant tastes or off-notes in the oral care compositions.

Consequently, there is a substantial need for the development of a non-alcoholic oral care composition with acceptable off-taste, and which has effective antimicrobial efficacy with respect to prevention or reduction of bad breath, the killing of oral bacteria or elimination or reduction of plaque.

SUMMARY

One aspect presented herein, provides an oral care composition, comprising:
a) a bioactive component in an amount from 0.01 to 10 wt % of the oral care composition;
b) a non-ionic surfactant comprising (i) a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan, and (ii) a surfactant selected from the group consisting of polyol esters and sugar esters;
c) at least one orally acceptable solvent; and optionally,
d) a $C_2$-$C_4$ monohydric alcohol,
wherein the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:10 to 10:1; and
wherein the ratio of the non-ionic surfactant to the bioactive component is from 0.5 to 3.

In one aspect, the oral care composition further comprises a flavor oil.

In one aspect, the amount of the $C_2$-$C_4$ monohydric alcohol is from 0 to 10 wt % of the oral care composition.

In one aspect, the amount of the $C_2$-$C_4$ monohydric alcohol is from 0 to 5 wt % of the oral care composition.

In one aspect, the oral care composition does not comprise the $C_2$-$C_4$ monohydric alcohol.

In one aspect, the poly(oxyethylene)-poly(oxypropylene)-poly(oxyethylene) block copolymer is the hydrophilic non-ionic surfactant sold under the tradename Poloxamer 407, comprising a triblock copolymer consisting of a central hydrophobic block of polypropylene glycol flanked by two hydrophilic blocks of polyethylene glycol (PEG).

In one aspect, the poly(oxyethylene)-modified fatty acid monoester of sorbitan is Tween 80.

In one aspect, the poly(oxyethylene)-modified fatty acid monoester of sorbitan is Tween 20.

In one aspect, the sugar ester is selected from the group consisting of: sucrose laurate, sucrose monolaurate, sucrose palmitate, sucrose monopalmitate, and combinations thereof.

In one aspect, the sugar ester is a sucrose ester. In an alternate aspect, the sugar ester is a fructose ester.

In one aspect, the polyol ester is a glycerol ester.

In one aspect, the polyol ester is monolauric acid decaglycerin ester.

In one aspect, the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:5 to 5:1.

In one aspect, the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:3 to 3:1.

In one aspect, the orally acceptable solvent is selected from the group consisting of: water, polyol, sugar alcohols, a $C_{1-6}$ linear or branched alkyl lactate, triacetine, triethylcitrate, benzylic alcohol, and combinations thereof.

In one aspect, the polyol is selected from the group consisting of: polyhydric alcohols, polyalkylene glycols, polyhydric alcohol esters, polyhydric alcohol ethers, and combinations thereof.

In one aspect, the polyhydric alcohol is selected from the group consisting of: glycerol, butylene glycol, hexylene glycol, 1,3-propanediol, propylene glycol, and combinations thereof.

In one aspect, the polyhydric alcohol is propylene glycol.

In one aspect, the polyhydric alcohol ester and polyhydric alcohol ether are selected from the group consisting of: dipropylene glycol, ethoxydiglycol, and combinations thereof.

In one aspect, the polyalkylene glycol is selected from the group consisting of: polyethylene glycol, polypropylene glycol, and combinations thereof.

In one aspect, the sugar alcohol is selected from the group consisting of: xylitol, sorbitol, mannitol, maltitol, inositol, allitol, altritol, dulcitol, galactitol, glucitol, hexitol, iditol, pentitol, ribitol, erythritol and mixtures thereof.

In one aspect, the sugar alcohol is selected from the group consisting of sorbitol and xylitol or mixtures thereof.

In one aspect, the $C_{1-6}$ linear or branched alkyl lactate is ethyl lactate.

One aspect presented herein provides a method for treating plaque, gingivitis or gum disease in a subject in need thereof, comprising the step of applying to the tissues of the oral cavity of the subject, an amount of the composition according to the aspects presented herein effective to reduce symptoms associated with plaque, gingivitis or gum disease.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Without intending to be limited to any particular theory, the solubility of essential oils in alcohol-free oral care compositions is limited, due to the low solubility of the essential oils in water. The low solubility of the essential oils may lead to an undesirable cloudy oral care composition. One solution to this problem is to form micro-emulsions of the essential oils, resulting in transparent or translucent oral care compositions. High amounts of surfactants are usually required to form micro-emulsions of essential oils in typical alcohol-free oral care compositions. However, the use of high amounts of surfactants is undesirable, as it reduces the antimicrobial efficacy of the oral care composition, and may cause unpleasant taste or off-notes.

The present disclosure provides personal care products intended for use on the oral cavity. In some aspects, the present disclosure provides transparent or translucent alcohol-free or slightly alcoholic oral care compositions which contain low amounts of surfactants and have high antimicrobial efficacy, having acceptable off-taste and organoleptic properties.

In some aspects, the oral care compositions presented comprise combinations of non-ionic surfactant or mixtures thereof that contain a polyoxyethylene (POE) group and have a hydrophilic-lipophilic balance (HLB) greater than or equal to 12, alternatively greater than or equal to 15, and another non-ionic surfactant or mixtures thereof chosen from the group of polyol esters and sugar esters.

Without intending to be limited to any particular theory, the solubility of oils can be enhanced by combining surfactants with different hydrophobicity. In selecting the surfactant for such systems, the surfactant's hydrophilic-lipophilic balance (HLB) is traditionally is considered. The HLB scale is based on the relative percentage of hydrophilic to lipophilic groups in the surfactant molecule. For example, an Oil-in-Water (O/W) emulsion would require a high HLB value (e.g., 10-18) to solubilize the molecules in water. The HLB scale by itself, however, fails to indicate whether a specific surfactant will be effective as a solubilization agent for active ingredients in a colloidal system, where other compounds, e.g., alcohol, salt and temperature usually affect the balance of the system. In such situations, where the colloidal dispersion system includes active ingredients, the balance of the system should be considered to reach high oil solubility. Specifically, the characteristic curvature of surfactants should match the hydrophobicity of oils in a specific system.

The present disclosure provides an oral care composition containing a non-ionic surfactant component comprising (i) a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan, and (ii) a surfactant selected from the group consisting of polyol esters and sugar esters, having a high antimicrobial efficacy, having acceptable off-taste and organoleptic properties. Without intending to be limited to any particular theory, the combination of the surfactant and the polyol ester or sugar ester give high solublization capacity for the active ingredients.

Accordingly, one aspect presented herein, provides an oral care composition, comprising:

a) a bioactive component in an amount from 0.01 to 10 wt % of the oral care composition;

b) a non-ionic surfactant comprising (i) a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan, and (ii) a surfactant selected from the group consisting of polyol esters and sugar esters;

c) at least one orally acceptable solvent; and optionally, d) a $C_2$-$C_4$ monohydric alcohol, wherein the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:10 to 10:1; and wherein the ratio of the non-ionic surfactant to the bioactive component is from 0.5 to 3.

As used herein, the term "oral care composition" refers to a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, solutions, mousse, foam, denture care product, mouth spray, lozenge or chewable tablet. The oral care composition may also be incorporated onto floss, strips or films for direct application or attachment to oral surfaces or integrated into a device or applicator such as a toothbrush or roll-ons. Such applicators may be for single or multiple use.

As used herein, the term "dentifrice" includes paste, gel, or liquid formulations unless otherwise specified. The dentifrice composition may be a single phase composition or may be a combination of two or more separate dentifrice compositions. The dentifrice composition may be in any desired form, such as deep striped, surface striped, multi-layered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, the term "dispenser" refers to any pump, tube, or container suitable for dispensing compositions such as dentifrices.

The phrase "reduced level" of alcohol means an amount of a $C_2$-$C_4$ monohydric alcohol up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total oral care composition. In some aspects, the oral care compositions of the present disclosure are free of $C_2$-$C_4$ monohydric alcohols.

It has been shown that microemulsions according to the present disclosure are transparent at room temperature (RT). The term transparent means that the microemulsions in the absence of coloring or fluorescent agents have nephelometric turbidity units (NTU) below 20 NTU, alternatively below 10 NTU, alternatively below 8 NTU.

The Bioactive Component

In some aspects, the oral care composition comprises a bioactive component. In some aspects, the amount of the bioactive component in the oral care composition is from 0.01 to 10 wt % of the oral care composition. Alternatively, in some aspects, the amount of the bioactive component in the oral care composition is from 0.01 to 9 wt % of the oral care composition. Alternatively, in some aspects, the amount of the bioactive component in the oral care composition is from 0.01 to 8 wt % of the oral care composition. Alternatively, in some aspects, the amount of the bioactive component in the oral care composition is from 0.01 to 7 wt % of the oral care composition. Alternatively, in some aspects, the amount of the bioactive component in the oral care composition is from 0.01 to 6 wt % of the oral care composition. Alternatively, in some aspects, the amount of the bioactive component in the oral care composition is from 0.01 to 5 wt % of the oral care composition. Alternatively, in some aspects, the amount of the bioactive component in the oral care composition is from 0.01 to 4 wt % of the oral care composition. Alternatively, in some aspects, the amount of the bioactive component in the oral care composition is from 0.01 to 3 wt % of the oral care composition. Alternatively, in some aspects, the amount of the bioactive component in the oral care composition is from 0.01 to 2 wt % of the oral care composition. Alternatively, in some aspects, the amount of the bioactive component in the oral care composition is from 0.01 to 1 wt % of the oral care composition. Alternatively, in some aspects, the amount of the bioactive component in the oral care composition is from 0.01 to 0.9 wt % of the oral care composition. Alternatively, in some aspects, the amount of the bioactive component in the oral care composition is from 0.01 to 0.8 wt % of the oral care composition. Alternatively, in some aspects, the amount of the bioactive component in the oral care composition is from 0.01 to 0.7 wt % of the oral care composition. Alternatively, in some aspects, the amount of the bioactive component in the oral care composition is from 0.01 to 0.6 wt % of the oral care composition. Alternatively, in some aspects, the amount of the bioactive component in the oral care composition is from 0.01 to 0.5 wt % of the oral care composition. Alternatively, in some aspects, the amount of the bioactive component in the oral care composition is from 0.01 to 0.4 wt % of the oral care composition. Alternatively, in some aspects, the amount of the bioactive component in the oral care composition is from 0.01 to 0.3 wt % of the oral care composition. Alternatively, in some aspects, the amount of the bioactive component in the oral care composition is from 0.01 to 0.2 wt % of the oral care composition. Alternatively, in some aspects, the amount of the bioactive component in the oral care composition is from 0.01 to 0.1 wt % of the oral care composition. Alternatively, in some aspects, the amount of the bioactive component in the oral care composition is from 0.01 to 0.09 wt % of the oral care composition. Alternatively, in some aspects, the amount of the bioactive component in the oral care composition is from 0.01 to 0.08 wt % of the oral care composition. Alternatively, in some aspects, the amount of the bioactive component in the oral care composition is from 0.01 to 0.07 wt % of the oral care composition. Alternatively, in some aspects, the amount of the bioactive component in the oral care composition is from 0.01 to 0.06 wt % of the oral care composition. Alternatively, in some aspects, the amount of the bioactive component in the oral care composition is from 0.01 to 0.05 wt % of the oral care composition. Alternatively, in some aspects, the amount of the bioactive component in the oral care composition is from 0.01 to 0.04 wt % of the oral care composition. Alternatively, in some aspects, the amount of the bioactive component in the oral care composition is from 0.01 to 0.03 wt % of the oral care composition. Alternatively, in some aspects, the amount of the bioactive component in the oral care composition is from 0.01 to 0.02 wt % of the oral care composition.

In some aspects, the amount of the bioactive component in the oral care composition is from 0.02 to 10 wt % of the oral care composition. Alternatively, in some aspects, the amount of the bioactive component in the oral care composition is from 0.03 to 10 wt % of the oral care composition. Alternatively, in some aspects, the amount of the bioactive component in the oral care composition is from 0.04 to 10 wt % of the oral care composition. Alternatively, in some aspects, the amount of the bioactive component in the oral care composition is from 0.05 to 10 wt % of the oral care composition. Alternatively, in some aspects, the amount of the bioactive component in the oral care composition is from 0.06 to 10 wt % of the oral care composition. Alternatively, in some aspects, the amount of the bioactive component in the oral care composition is from 0.07 to 10 wt % of the oral care composition. Alternatively, in some aspects, the amount of the bioactive component in the oral care composition is from 0.08 to 10 wt % of the oral care composition. Alternatively, in some aspects, the amount of the bioactive component in the oral care composition is from 0.09 to 10 wt % of the oral care composition. Alternatively, in some aspects, the amount of the bioactive component in the oral care composition is from 0.1 to 10 wt % of the oral care composition. Alternatively, in some aspects, the amount of the bioactive component in the oral care composition is from 0.2 to 10 wt % of the oral care composition. Alternatively, in some aspects, the amount of the bioactive component in the oral care composition is from 0.3 to 10 wt % of the oral care composition. Alternatively, in some aspects, the amount of the bioactive component in the oral care composition is from 0.4 to 10 wt % of the oral care composition. Alternatively, in some aspects, the amount of the bioactive component in the oral care composition is from 0.5 to 10 wt % of the oral care composition. Alternatively, in some aspects, the amount of the bioactive component in the oral care composition is from 0.6 to 10 wt % of the oral care composition. Alternatively, in some aspects, the amount of the bioactive component in the oral care composition is from 0.7 to 10 wt % of the oral care composition. Alternatively, in some aspects, the amount of the bioactive component in the oral care composition is from 0.8 to 10 wt % of the oral care composition. Alternatively, in some aspects, the amount of the bioactive component in the oral care composition is from 0.9 to 10 wt % of the oral care composition. Alternatively, in some aspects, the amount of the bioactive component in the oral care composition is from 1 to 10 wt % of the oral care composition. Alternatively, in some aspects, the amount of the bioactive component in the oral care composition is from 2 to 10 wt % of the oral care composition. Alternatively, in some aspects, the amount of the bioactive component in the oral care composition is from 3 to 10 wt % of the oral care composition. Alternatively, in some aspects, the amount of the bioactive component in the oral care composition is from 4 to 10 wt % of the oral care composition. Alternatively, in some aspects, the amount of the bioactive component in the oral care composition is from 5 to 10 wt % of the oral care composition. Alternatively, in some aspects, the amount of the bioactive component in the oral care composition is from 6 to 10 wt % of the oral care composition. Alternatively, in some aspects, the amount of the bioactive component in the oral care composition is from 7 to 10 wt % of the oral care composition. Alternatively, in some aspects, the amount of the bioactive component in the oral care composition is from 8 to 10 wt % of the oral care composition. Alternatively, in some aspects, the amount of the bioactive component in the oral care composition is from 9 to 10 wt % of the oral care composition.

In some aspects, the amount of the bioactive component in the oral care composition is 0.01, or 0.02, or 0.03, or 0.04, or 0.05, or 0.06, or 0.07, or 0.08, or 0.09, or 0.1, or 0.2, or 0.3, or 0.4, or 0.5, or 0.6, or 0.7, or 0.8, or 0.9, or 1, or 2, or 3, or 4, or 5, or 6, or 7, or 8, or 9, or 10 wt % of the oral care composition.

As used herein, the term "bioactive component" refers to at least one water-insoluble agent that imparts at least one activity selected from the group consisting of: an anticaries activity, an antiplaque activity, an antigingivitis activity or a gum disease treatment, an antimicrobial activity, and a flavor.

In some embodiments, the bioactive component is an essential oil. Non-limiting examples of essential oils include: Thymol, [$(CH_3)_2CHC_6H_3(CH_3)OH$, also known as isopropyl-m-cresol], Methyl salicylate, [$C_6H_4OHCOOCH_3$, also known as wintergreen oil], Eucalyptol ($C_{10}H_{18}O$, also known as cineol), and Menthol ($CH_3C_6H_9(C_3H_7)OH$), also known as hexahydrothymol).

In some embodiments, the bioactive component is at least one agent selected from the group consisting of: menthol, methyl salicylate, thymol and eucalyptol. In some aspects, the bioactive component comprises menthol, methyl salicylate, thymol and eucalyptol.

In some aspects, the bioactive component comprises at least one bioactive agent disclosed in U.S. Patent Application Publication No. 2016/01425203.

In some aspects, the bioactive component comprises at least one bioactive agent disclosed in U.S. Patent Application Publication No. 2015/0306007.

In some aspects, the bioactive component comprises at least one bioactive agent disclosed in U.S. Patent Application Publication No. 2007/0190080.

In some aspects, the bioactive component comprises at least one bioactive agent disclosed in U.S. Patent Application Publication No. 2014/0242003.

In some aspects, the bioactive component comprises at least one bioactive agent disclosed in U.S. Patent Application Publication No. 2014/0286880.

In some aspects, the bioactive component comprises at least one bioactive agent disclosed in U.S. Patent Application Publication No. 2013/0280180.

In some aspects, the bioactive component comprises at least one bioactive agent disclosed in U.S. Pat. No. 6,348,187.

In some aspects, the bioactive component comprises at least one bioactive agent disclosed in U.S. Pat. No. 5,817,295.

In some aspects, the bioactive component comprises at least one bioactive agent disclosed in U.S. Pat. No. 5,292,527.

The Non-Ionic Surfactant Component

In some aspects, the oral care composition comprises a non-ionic surfactant component, comprising (i) a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan, and (ii) a surfactant selected from the group consisting of polyol esters and sugar esters.

In some aspects, the ratio of the non-ionic surfactant to the bioactive component is from 0.5 to 3. Alternatively, in some aspects, the ratio of the non-ionic surfactant to the bioactive component is from 0.6 to 3. Alternatively, in some aspects, the ratio of the non-ionic surfactant to the bioactive component is from 0.6 to 3. Alternatively, in some aspects, the ratio of the non-ionic surfactant to the bioactive component is from 0.8 to 3. Alternatively, in some aspects, the ratio of the non-ionic surfactant to the bioactive component is from 0.9 to 3. Alternatively, in some aspects, the ratio of the non-ionic surfactant to the bioactive component is from 1 to 3. Alternatively, in some aspects, the ratio of the non-ionic surfactant to the bioactive component is from 1.1 to 3. Alternatively, in some aspects, the ratio of the non-ionic surfactant to the bioactive component is from 1.2 to 3. Alternatively, in some aspects, the ratio of the non-ionic surfactant to the bioactive component is from 1.3 to 3. Alternatively, in some aspects, the ratio of the non-ionic surfactant to the bioactive component is from 1.4 to 3. Alternatively, in some aspects, the ratio of the non-ionic surfactant to the bioactive component is from 1.5 to 3.

Alternatively, in some aspects, the ratio of the non-ionic surfactant to the bioactive component is from 1.6 to 3. Alternatively, in some aspects, the ratio of the non-ionic surfactant to the bioactive component is from 1.7 to 3. Alternatively, in some aspects, the ratio of the non-ionic surfactant to the bioactive component is from 1.8 to 3. Alternatively, in some aspects, the ratio of the non-ionic surfactant to the bioactive component is from 1.9 to 3. Alternatively, in some aspects, the ratio of the non-ionic surfactant to the bioactive component is from 2 to 3. Alternatively, in some aspects, the ratio of the non-ionic surfactant to the bioactive component is from 2.1 to 3. Alternatively, in some aspects, the ratio of the non-ionic surfactant to the bioactive component is from 2.2 to 3. Alternatively, in some aspects, the ratio of the non-ionic surfactant to the bioactive component is from 2.3 to 3. Alternatively, in some aspects, the ratio of the non-ionic surfactant to the bioactive component is from 2.4 to 3. Alternatively, in some aspects, the ratio of the non-ionic surfactant to the bioactive component is from 2.5 to 3. Alternatively, in some aspects, the ratio of the non-ionic surfactant to the bioactive component is from 2.6 to 3. Alternatively, in some aspects, the ratio of the non-ionic surfactant to the bioactive component is from 2.7 to 3. Alternatively, in some aspects, the ratio of the non-ionic surfactant to the bioactive component is from 2.8 to 3. Alternatively, in some aspects, the ratio of the non-ionic surfactant to the bioactive component is from 2.9 to 3.

In some aspects, the ratio of the non-ionic surfactant to the bioactive component is from 0.5 to 2.9. Alternatively, in some aspects, the ratio of the non-ionic surfactant to the bioactive component is from 0.5 to 2.8. Alternatively, in some aspects, the ratio of the non-ionic surfactant to the bioactive component is from 0.5 to 2.7. Alternatively, in some aspects, the ratio of the non-ionic surfactant to the bioactive component is from 0.5 to 2.6. Alternatively, in some aspects, the ratio of the non-ionic surfactant to the bioactive component is from 0.5 to 2.5. Alternatively, in some aspects, the ratio of the non-ionic surfactant to the bioactive component is from 0.5 to 2.4. Alternatively, in some aspects, the ratio of the non-ionic surfactant to the bioactive component is from 0.5 to 2.3. Alternatively, in some aspects, the ratio of the non-ionic surfactant to the bioactive component is from 0.5 to 2.2. Alternatively, in some aspects, the ratio of the non-ionic surfactant to the bioactive component is from 0.5 to 2.1. Alternatively, in some aspects, the ratio of the non-ionic surfactant to the bioactive component is from 0.5 to 2. Alternatively, in some aspects, the ratio of the non-ionic surfactant to the bioactive component is from 0.5 to 1.9. Alternatively, in some aspects, the ratio of the non-ionic surfactant to the bioactive component is from 0.5 to 1.8. Alternatively, in some aspects, the ratio of the non-ionic surfactant to the bioactive component is from 0.5 to 1.7. Alternatively, in some aspects, the ratio of the non-ionic surfactant to the bioactive component is from 0.5 to 1.6. Alternatively, in some aspects, the ratio of the non-ionic surfactant to the bioactive component is from 0.5 to 1.5. Alternatively, in some aspects, the ratio of the non-ionic surfactant to the bioactive component is from 0.5 to 1.4. Alternatively, in some aspects, the ratio of the non-ionic surfactant to the bioactive component is from 0.5 to 1.3. Alternatively, in some aspects, the ratio of the non-ionic surfactant to the bioactive component is from 0.5 to 1.2. Alternatively, in some aspects, the ratio of the non-ionic surfactant to the bioactive component is from 0.5 to 1.1. Alternatively, in some aspects, the ratio of the non-ionic surfactant to the bioactive component is from 0.5 to 1. Alternatively, in some aspects, the ratio of the non-ionic surfactant to the bioactive component is from 0.5 to 0.9. Alternatively, in some aspects, the ratio of the non-ionic surfactant to the bioactive component is from 0.5 to 0.8. Alternatively, in some aspects, the ratio of the non-ionic surfactant to the bioactive component is from 0.5 to 0.7. Alternatively, in some aspects, the ratio of the non-ionic surfactant to the bioactive component is from 0.5 to 0.6.

In some aspects, the ratio of the non-ionic surfactant to the bioactive component is 0.5, 0.6, or 0.7, or 0.8, or 0.9, or 1, or 1.1, or 1.2, or 1.3, or 1.4, or 1.5, or 1.6, or 1.7, or 1.8, or 1.9, or 2, or 2.1, or 2.2, or 2.3, or 2.4, or 2.5, or 2.6, or 2.7, or 2.8, or 2.9, or 3.

In some aspects, the poly(oxyethylene)-poly(oxypropylene)-poly(oxyethylene) block copolymer is the hydrophilic non-ionic surfactant sold under the tradename Poloxamer 407, comprising a triblock copolymer consisting of a central hydrophobic block of polypropylene glycol flanked by two hydrophilic blocks of polyethylene glycol (PEG).

In some aspects, the poly(oxyethylene)-poly(oxypropylene)-poly(oxyethylene) block copolymer is the hydrophilic non-ionic surfactant sold under the tradename Kolliphor 40, comprising poly(oxyethylene) hydrogenated castor oil.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Patent Application Publication No. 2016/01425203.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Patent Application Publication No. 2015/0306007.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Patent Application Publication No. 2014/0242003.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Patent Application Publication No. 2014/0286880.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Pat. No. 5,817,295.

In some aspects, the poly(oxyethylene)-poly(oxypropylene)-poly(oxyethylene) block copolymer comprises at least one poly(oxyethylene)-poly(oxypropylene)-poly(oxyethylene) block copolymer disclosed in U.S. Pat. No. 5,292,527.

In some aspects, the poly(oxyethylene)-modified fatty acid monoester of sorbitan is Tween 80.

In some aspects, the poly(oxyethylene)-modified fatty acid monoester of sorbitan is Tween 20.

In some aspects, the sugar ester is selected from the group consisting of: sucrose laurate, sucrose monolaurate, sucrose palmitate, sucrose monopalmitate, and combinations thereof.

In some aspects, the sugar ester is a sucrose ester. In an alternate aspect, the sugar ester is a fructose ester.

In some aspects, the polyol ester is a glycerol ester.

In some aspects, the polyol ester is monolauric acid decaglycerin ester.

In some aspects, the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:5 to 5:1.

In some aspects, the ratio of the surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan to the surfactant selected from the group consisting of polyol esters and sugar esters is from 1:3 to 3:1.

Flavor Systems

In some aspects, the composition further comprises a flavor system. The flavor system may mask any unpleasant taste and sensations due to certain components of the composition such as antimicrobial actives or peroxide. Without intending to be limited to any particular theory, pleasant tasting compositions improve user compliance to prescribed or recommended use of oral care products. The present flavor system may also comprise traditional flavor components, in particular those that are relatively stable in the presence of usual oral care product carrier materials or excipients. The combination of the selected flavoring system with the compositions presented herein may provide a high-impact refreshing sensation with a well-rounded flavor profile.

In some aspects, the flavor system may comprise additional flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, gamma undecalactone and mixtures thereof.

Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents may generally be used in the compositions at levels of from about 0.001% to about 5%, by weight of the composition.

In some aspects, the flavor system may further include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used.

In some aspects, the composition may contains from about 0.1% to about 10% of sweetener, alternatively from about 0.1% to about 1%, by weight of the composition.

In some aspects, the flavor system may further include salivating agents, warming agents, and numbing agents. These agents may be present in the compositions at a level of from about 0.001% to about 10%, alternatively from about 0.1% to about 1%, by weight of the composition.

Suitable salivating agents include Jambu® manufactured by Takasago. Suitable numbing agents include benzocaine, lidocaine, clove bud oil, and ethanol. Examples of warming agents include ethanol, capsicum and nicotinate esters, such as benzyl nicotinate.

In addition to the components described above, the present compositions may comprise additional optional components and/or orally acceptable carrier materials.

Orally Acceptable Solvents

In some aspects, the amount of the orally acceptable solvent in the oral care composition is from 1 to 95 wt % of the oral care composition. Alternatively, the amount of the orally acceptable solvent in the oral care composition is from 1 to 90 wt % of the oral care composition. Alternatively, the amount of the orally acceptable solvent in the oral care composition is from 1 to 85 wt % of the oral care composition. Alternatively, the amount of the orally acceptable solvent in the oral care composition is from 1 to 80 wt % of the oral care composition. Alternatively, the amount of the orally acceptable solvent in the oral care composition is from 1 to 75 wt % of the oral care composition. Alternatively, the amount of the orally acceptable solvent in the oral care composition is from 1 to 70 wt % of the oral care composition. Alternatively, the amount of the orally acceptable solvent in the oral care composition is from 1 to 65 wt % of the oral care composition. Alternatively, the amount of the orally acceptable solvent in the oral care composition is from 1 to 60 wt % of the oral care composition. Alternatively, the amount of the orally acceptable solvent in the oral care composition is from 1 to 55 wt % of the oral care composition. Alternatively, the amount of the orally acceptable solvent in the oral care composition is from 1 to 50 wt % of the oral care composition. Alternatively, the amount of the orally acceptable solvent in the oral care composition is from 1 to 45 wt % of the oral care composition. Alternatively, the amount of the orally acceptable solvent in the oral care composition is from 1 to 40 wt % of the oral care composition. Alternatively, the amount of the orally acceptable solvent in the oral care composition is from 1 to 35 wt % of the oral care composition. Alternatively, the amount of the orally acceptable solvent in the oral care composition is from 1 to 95 wt % of the oral care composition. Alternatively, the amount of the orally acceptable solvent in the oral care composition is from 1 to 25 wt % of the oral care composition. Alternatively, the amount of the orally acceptable solvent in the oral care composition is from 1 to 20 wt % of the oral care composition. Alternatively, the amount of the orally acceptable solvent in the oral care composition is from 1 to 15 wt % of the oral care composition. Alternatively, the amount of the orally acceptable solvent in the oral care composition is from 1 to 10 wt % of the oral care composition. Alternatively, the amount of the orally acceptable solvent in the oral care composition is from 1 to 9 wt % of the oral care composition. Alternatively, the amount of the orally acceptable solvent in the oral care composition is from 1 to 8 wt % of the oral care composition. Alternatively, the amount of the orally acceptable solvent in the oral care composition is from 1 to 7 wt % of the oral care composition. Alternatively, the amount of the orally acceptable solvent in the oral care composition is from 1 to 6 wt % of the oral care composition. Alternatively, the amount of the orally acceptable solvent in the oral care composition is from 1 to 5 wt % of the oral care composition. Alternatively, the amount of the orally acceptable solvent in the oral care composition is from 1 to 4 wt % of the oral care composition. Alternatively, the amount of the orally acceptable solvent in the oral care composition is from 1 to 3 wt % of the oral care composition. Alternatively, the amount of the orally acceptable solvent in the oral care composition is from 1 to 2 wt % of the oral care composition.

In some aspects, the amount of the orally acceptable solvent in the oral care composition is from 2 to 95 wt % of the oral care composition. Alternatively, the amount of the orally acceptable solvent in the oral care composition is from 3 to 95 wt % of the oral care composition. Alternatively, the amount of the orally acceptable solvent in the oral care composition is from 4 to 95 wt % of the oral care composition. Alternatively, the amount of the orally acceptable solvent in the oral care composition is from 5 to 95 wt % of the oral care composition. Alternatively, the amount of the orally acceptable solvent in the oral care composition is from 6 to 95 wt % of the oral care composition. Alternatively, the amount of the orally acceptable solvent in the oral care composition is from 7 to 95 wt % of the oral care composition. Alternatively, the amount of the orally acceptable solvent in the oral care composition is from 8 to 95 wt % of the oral care composition. Alternatively, the amount of the orally acceptable solvent in the oral care composition is from 9 to 95 wt % of the oral care composition. Alternatively, the amount of the orally acceptable solvent in the oral care composition is from 10 to 95 wt % of the oral care composition. Alternatively, the amount of the orally acceptable solvent in the oral care composition is from 15 to 95 wt % of the oral care composition. Alternatively, the amount of the orally acceptable solvent in the oral care composition is from 20 to 95 wt % of the oral care composition. Alternatively, the amount of the orally acceptable solvent in the oral care composition is from 25 to 95 wt % of the oral care composition. Alternatively, the amount of the orally acceptable solvent in the oral care composition is from 30 to 95 wt % of the oral care composition. Alternatively, the amount of the orally acceptable solvent in the oral care composition is from 35 to 95 wt % of the oral care composition. Alternatively, the amount of the orally acceptable solvent in the oral care composition is from 40 to 95 wt % of the oral care composition. Alternatively, the amount of the orally acceptable solvent in the oral care composition is from 45 to 95 wt % of the oral care composition. Alternatively, the amount of the orally acceptable solvent in the oral care composition is from 50 to 95 wt % of the oral care composition. Alternatively, the amount of the orally acceptable solvent in the oral care composition is from 55 to 95 wt % of the oral care composition. Alternatively, the amount of the orally acceptable solvent in the oral care composition is from 60 to 95 wt % of the oral care composition. Alternatively, the amount of the orally acceptable solvent in the oral care composition is from 65 to 95 wt % of the oral care composition. Alternatively, the amount of the orally acceptable solvent in the oral care composition is from 70 to 95 wt % of the oral care composition. Alternatively, the amount of the orally acceptable solvent in the oral care composition is from 75 to 95 wt % of the oral care composition. Alternatively, the amount of the orally acceptable solvent in the oral care composition is from 80 to 95 wt % of the oral care composition. Alternatively, the amount of the orally acceptable solvent in the oral care composition is from 85 to 95 wt % of the oral care composition. Alternatively, the amount of the orally acceptable solvent in the oral care composition is from 90 to 95 wt % of the oral care composition.

In some aspects, the amount of the orally acceptable solvent in the oral care composition is 1, or 2, or 3, or 4, or 5, or 6, or 7, or 8, or 9, or 10, or 15, or 20, or 25, or 30, or 40, or 45, or 50, or 55, or 60, or 65, or 70, or 75, or 80, or 85, or 90, or 95 wt % of the oral care composition.

In some aspects, the orally acceptable solvent is selected from the group consisting of: water, polyol, sugar alcohols, a $C_{1-6}$ linear or branched alkyl lactate, triacetine, triethylcitrate, benzylic alcohol, and combinations thereof.

In some aspects, the polyol is selected from the group consisting of: polyhydric alcohols, polyalkylene glycols, polyhydric alcohol esters, polyhydric alcohol ethers, and combinations thereof.

In some aspects, the polyhydric alcohol is selected from the group consisting of: glycerol, butylene glycol, hexylene glycol, 1,3-propanediol, propylene glycol, and combinations thereof.

In some aspects, the polyhydric alcohol is propylene glycol.

In some aspects, the polyhydric alcohol ester and polyhydric alcohol ether are selected from the group consisting of: dipropylene glycol, ethoxydiglycol, and combinations thereof.

In some aspects, the polyalkylene glycol is selected from the group consisting of: polyethylene glycol, polypropylene glycol, and combinations thereof.

In some aspects, the sugar alcohol is selected from the group consisting of: xylitol, sorbitol, mannitol, maltitol, inositol, allitol, altritol, dulcitol, galactitol, glucitol, hexitol, iditol, pentitol, ribitol, erythritol and mixtures thereof.

In some aspects, the sugar alcohol is selected from the group consisting of sorbitol and xylitol or mixtures thereof.

In some aspects, the $C_{1-6}$ linear or branched alkyl lactate is ethyl lactate.

Additional Optional Components

The oral care compositions of the present disclosure may also include one or more optional ingredients nonexclusively including a thickening agent, colorants, additional humectants, chelating agents, cooling agents, whitening agents, and additives such as preservatives, pH adjusting agents, and the like.

In some aspects, the pH of the oral care compositions of the present disclosure is maintained at range of below 5 (or about 5), alternatively, below 4.5 (or about 4.5) or, alternatively, in the range of from 4.4 (or about 4.4) to 3 (or about 3), or alternatively in the range of from 3.5 (or about 3.5) to 4.4 (or about 4.4).

In some aspects, the pH of the oral care composition may be adjusted by the addition of an amount of benzoic acid to adjust the pH of the oral care composition to the desired pH.

In some aspects, the effective amount of the sodium benzoate is from 0 to 0.2 wt % of the oral care composition. In some aspects, the effective amount of the sodium benzoate is from 0.05 to 0.1 wt % of the oral care composition.

Commercially available thickening agents, which are capable of imparting the appropriate viscosity to the compositions, are suitable for use in the oral care compositions presented herein. Examples of suitable thickening agents nonexclusively include: mono or diesters of 1) polyethylene glycol of formula: $HO—(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Illinois or from Comiel, S.p.A. of Bologna, Italy under the trade name, "PEG 6000 DS".

Examples of suitable chelating agents include those which are capable of protecting and preserving the oral care compositions according to the aspects presented herein. In some aspects, the chelating agent is ethylenediamine tetracetic acid ("EDTA"), alternatively tetrasodium EDTA, available commercially from Dow Chemical Company of Midland, Mich. under the trade name, "Versene 100XL" and is present in an amount, based upon the total weight of the composition, from about 0 to about 0.5 wt %, alternatively from about 0.05 wt % to about 0.25 wt %.

Suitable preservatives include, but are not limited to, sodium benzoate, and polysorbate and are present in the composition in an amount, based upon the total weight of the composition, from about 0 to about 0.2 wt %, alternatively from about 0.05 wt % to about 0.10 wt %.

In some aspects, the oral care composition comprises at least one cooling compound. Cooling compounds or compounds that have a physiological cooling effect on oral surfaces are common ingredients in a wide variety of products including edible compositions and personal care products and in flavor or perfume compositions for use in such products. Examples of edible compositions include confectionery, candies, chocolate, chewing gum, beverages and oral medicines. A class of topically applied compositions to which the present disclosure relates is for oral and throat care, which include products in powder, paste or liquid forms and which on being used are retained for a time sufficient to contact the surface and the internal mucous membrane of the oral cavities or the pharynx. Such products include for example, mouthwashes, dental and throat lozenges, gargles, chewing gum, dentifrice or toothpastes, toothpicks, dental tablets and powders and topical solutions for application in dental treatment, as well as cough-syrups, chewable antacids and digestion promoting preparations.

The pleasant cooling sensation provided by cooling compounds contributes to the appeal and acceptability of the products. In particular, oral care products such as dentifrices and mouthwashes are formulated with coolants because they provide breath freshening effects and a clean, cool, fresh feeling in the mouth.

Without intending to be limited to any particular theory, sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, one candidate involved in sensing cold has been identified and designated as cold- and menthol-sensitive receptor (CMR1) or TRPM8.

The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood.

Without intending to be limited to any particular theory, while it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing. For example, menthol is widely used as a cooling agent, but menthol can also produce other sensations including tingling, burning, prickling and stinging as well as a minty smell and bitter taste. Thus, it can be inferred that menthol, and other cooling agents may act on many different receptors, including cold, warm, pain and taste receptors.

However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. The present disclosure is thus based on the discovery of agents that can be used to enhance and/or modulate the activity of cooling and flavoring compounds.

Examples of cooling compounds suitable for inclusion into the oral care compositions according to certain aspects presented herein are disclosed in International Patent Application Publication No. WO2014090293.

Examples of cooling compounds suitable for inclusion into the oral care compositions according to certain aspects presented herein are disclosed in International Patent Application Publication No. WO2012061698.

Examples of cooling compounds suitable for inclusion into the oral care compositions according to certain aspects presented herein are disclosed in U.S. Patent Application Publication No. 2010007608.

Examples of cooling compounds suitable for inclusion into the oral care compositions according to certain aspects presented herein are disclosed in U.S. Patent Application Publication No. 20080319055.

Examples of cooling compounds suitable for inclusion into the oral care compositions according to certain aspects presented herein are disclosed in U.S. Patent Application Publication No. 20080311232.

Examples of cooling compounds suitable for inclusion into the oral care compositions according to certain aspects presented herein are disclosed in U.S. Patent Application Publication No. 20090054520.

Examples of cooling compounds suitable for inclusion into the oral care compositions according to certain aspects presented herein are disclosed in U.S. Patent Application Publication No. 20080177800.

Examples of cooling compounds suitable for inclusion into the oral care compositions according to certain aspects presented herein are disclosed in U.S. Patent Application Publication No. 20080096969.

Examples of cooling compounds suitable for inclusion into the oral care compositions according to certain aspects presented herein are disclosed in International Patent Application Publication No. WO2010128026.

Examples of cooling compounds suitable for inclusion into the oral care compositions according to certain aspects presented herein are disclosed in International Patent Application Publication No. WO2011061330.

Examples of cooling compounds suitable for inclusion into the oral care compositions according to certain aspects presented herein are disclosed in International Patent Application Publication No. WO2011138696.

Examples of cooling compounds suitable for inclusion into the oral care compositions according to certain aspects presented herein are disclosed in U.S. Pat. No. 8,377,422.

Examples of cooling compounds suitable for inclusion into the oral care compositions according to certain aspects presented herein are disclosed in International Patent Application Publication No. WO2013033501.

Examples of cooling compounds suitable for inclusion into the oral care compositions according to certain aspects presented herein are disclosed in U.S. Patent Application Publication No. 20130216486.

Examples of cooling compounds suitable for inclusion into the oral care compositions according to certain aspects presented herein are disclosed in U.S. Pat. No. 7,935,848.

Examples of cooling compounds suitable for inclusion into the oral care compositions according to certain aspects presented herein are disclosed in U.S. Patent Application Publication No. 20130345300.

Examples of cooling compounds suitable for inclusion into the oral care compositions according to certain aspects presented herein are disclosed in International Patent Application Publication No. WO2013080830.

Examples of cooling compounds suitable for inclusion into the oral care compositions according to certain aspects presented herein are disclosed in International Patent Application Publication No. WO2014010657.

Examples of cooling compounds suitable for inclusion into the oral care compositions according to certain aspects presented herein are disclosed in U.S. Patent Application Publication No. 20140219930.

Examples of cooling compounds suitable for inclusion into the oral care compositions according to certain aspects presented herein are disclosed in U.S. Patent Application Publication No. 20150139918.

In some aspects, the at least one cooling compound is selected from the group consisting of: 2-(4-ethylphenoxy)-N-(1H-pyrazol-5-yl)-N-(2-thienylmethyl)acetamide, WS-23 (2-Isopropyl-N,2,3-trimethylbutyramide), FEMA 3804; WS-3 (N-Ethyl-p-menthane-3-carboxamide), FEMA 3455; WS-5 [Ethyl 3-(p-menthane-3-carboxamido)acetate], FEMA 4309; WS-12 (1R,2S,5R)—N-(4-Methoxyphenyl)-p-menthanecarboxamide, FEMA 4681; WS-27 (N-Ethyl-2,2-diisopropylbutanamide), FEMA 4557; N-Cyclopropyl-5-methyl-2-isopropylcyclohexanecarboxamide, FEMA 4693, WS-116 (N-(1,1-Dimethyl-2-hydroxyethyl)-2,2-diethylbutanamide), N-(1,1-Dimethyl-2-hydroxyethyl)2,2-diethylbutanamide, FEMA 4603, Menthoxyethanol, FEMA 4154, N-(4-cyanomethylphenyl)-p-menthanecarboxamide, FEMA 4496; N-(2-(Pyridin-2-yl)ethyl)-3-p-menthanecarboxamide, FEMA 4549; N-(2-Hydroxyethyl)-2-isopropyl-2,3-dimethylbutanamide, FEMA 4602 and (also N-(4-(carbamoylmethyl)phenyl)-menthylcarboxamide, FEMA 4684; (1R,2S,5R)—N-(4-Methoxyphenyl)-p-menthanecarboxamide (WS-12), FEMA 4681; (2S,5R)—N-[4-(2-Amino-2-oxoethyl)phenyl]-p-menthanecarboxamide, FEMA 4684; and N-Cyclopropyl-5-methyl-2-isopropylcyclohexanecarbonecarboxamide, FEMA 4693; 2-[(2-p-Menthoxy)ethoxy]ethanol, FEMA 4718; (2,6-Diethyl-5-isopropyl-2-methyltetrahydropyran, FEMA 4680); trans-4-tert-Butylcyclohexanol, FEMA 4724; 2-(p-tolyloxy)-N-(1H-pyrazol-5-yl)-N-((thiophen-2-yl)methyl)acetamide, FEMA 4809; Menthone glycerol ketal, FEMA 3807; Menthone glycerol ketal, FEMA 3748; (−)-Menthoxypropane-1,2-diol; 3-(1-Menthoxy)-2-methylpropane-1,2-diol, FEMA 3849; Isopulegol; (+)-cis & (−)-trans p-Menthane-3,8-diol, Ratio ~62:38, FEMA 4053; 2,3-dihydroxy-p-menthane; 3,3,5-trimethylcyclohexanone glycerol ketal; menthyl pyrrolidone carboxylate; (1R,3R,4S)-3-menthyl-3,6-dioxaheptanoate; (1R,2S,5R)-3-menthyl methoxy acetate; (1R,2S,5R)-3-menthyl 3,6,9-trioxadecanoate; (1R,2S,5R)-3-menthyl 3,6,9-trioxadecanoate; (1R,2S,5R)-3-menthyl (2-hydroxyethoxy)acetate; (1R,2S,5R)-menthyl 11-hydroxy-3,6,9-trioxaundecanoate; Cubebol, FEMA 4497; N-(4-cyanomethylphenyl) p-menthanecarboxamide, FEMA 4496; 2-isopropyl-5-methylcyclohexyl 4-(dimethylamino)-4-oxobutanoate, FEMA 4230; N-(4-cyanomethylphenyl) p-menthanecarboxamide, FEMA 4496; N-(2-pyridin-2-ylethyl) p-menthanecarboxamide, FEMA 4549, Menthyl lactate, FEMA 3748; 6-isopropyl-3,9-dimethyl-1,4-dioxaspiro[4.5]decan-2-one, FEMA 4285; N-benzo[1,3]dioxol-5-yl-3-p-menthanecarboxamide; N-(1-isopropyl-1,2-dimethylpropyl)-1,3-benzodioxole-5-carboxamide; N—(R)-2-oxotetrahydrofuran-3-yl-(1R,2S,5R)-p-menthane-3-carboxamide; mixture of 2,2,5,6,6-pentamethyl-2,3,6,6a-tetrahydropentalen-3a(1H)-ol and 5-(2-hydroxy-2-methylpropyl)-3,4,4-trimethylcyclopent-2-en-1-one; (1R,2S,5R)-2-isopropyl-5-methyl-N-(2-(pyridin-2-yl)ethyl)cyclohexanecarboxamide, FEMA 4549; (2S,5R)-2-isopropyl-5-methyl-N-(2-(pyridin-4-yl)ethyl)cyclohexanecarboxamide; N-(4-cyanomethylphenyl) p-menthanecarboxamide, FEMA 4496; (1S,2S,5R)—N-(4-(cyanomethyl)phenyl)-2-isopropyl-5-methylcyclohexanecarboxamide; 1/7-isopropyl-4/5-methylbicyclo[2.2.2]oct-5-ene derivatives; 4-methoxy-N-phenyl-N-[2-(pyridin-2-yl)ethyl]benzamide; 4-methoxy-N-phenyl-N-[2-(pyridin-2-yl)ethyl]benzenesulfonamide; 4-chloro-N-phenyl-N-[2-(pyridin-2-yl)ethyl]benzenesulfonamide; 4-cyano-N-phenyl-N-[2-(pyridin-2-yl)ethyl]benzenesulfonamid; 4-((benzhydrylamino)methyl)-2-methoxyphenol; 4-((bis(4-methoxyphenyl)-methylamino)-methyl)-2-methoxyphenol; 4-((1,2-diphenylethylamino)methyl)-2-methoxyphenol; 4-((benzhydryloxy)methyl)-2-methoxyphenol, 4-((9H-fluoren-9-ylamino)methyl)-2-methoxyphenol; 4-((benzhydrylamino)methyl)-2-ethoxyphenol; 1-(4-methoxyphenyl)-2-(1-methyl-1H-benzo[d]imidazol-2-yl)vinyl4-methoxybenzoate; 2-(1-isopropyl-6-methyl-1H-benzo[d]imidazol-2-yl)-1-(4-methoxyphenyl)vinyl4-methoxybenzoate; (Z)-2-(1-isopropyl-5-methyl-1H-benzo[d]imidazol-2- yl)-1-(4-methoxy-phenyl)vinyl-4-methoxybenzoate; 3-alkyl-p-methan-3-ol derivatives; derivatives of fenchyl, D-bornyl, L-bornyl, exo-norbornyl, 2-methylisobornyl, 2-ethylfenchyl, 2-methylbornyl, cis-pinan-2-yl, verbanyl and isobornyl; menthyl oxamate derivatives; menthyl 3-oxocarboxylic acid esters; N alpha-(Menthanecarbonyl)amino acid amides; p-menthane carboxamide and WS-23 analogs; (−)-(1R,2R,4S)-dihydroumbellulol; p-menthane alkyloxy amides; cyclohexane derivatives; butone derivatives; a mixture of 3-menthoxy-1-propanol and 1-menthoxy-2-propanol; 1-[2-hydroxy phenyl]-4-[2-nitrophenyl-]-1,2,3,6-tetrahydropyrimidine-2-one; 4-methyl-3-(1-pyrrolidinyl)-2[5H]-furanone; and combinations thereof.

Orally Acceptable Carrier Materials and Products

In some aspects, the orally acceptable carrier may comprise one or more compatible solid or liquid excipients or diluents which are suitable for topical oral administration. By "compatible," as used herein, is meant that the components of the composition are capable of being commingled without interaction in a manner which would substantially reduce stability and/or efficacy.

The carriers or excipients of the present disclosure can include the usual and conventional components of dentifrices, non-abrasive gels, subgingival gels, mouthwashes or rinses, mouth sprays, chewing gums, lozenges and breath mints.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. Nos. 5,213,790; 5,145,666 and 5,281,410 all to Lukacovic et al., and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani. Carriers suitable for the preparation of compositions of the present disclosure are well known in the art. Their selection will depend on secondary considerations like taste, cost, and shelf stability, and the like.

Without intending to be limited to any particular theory, the compositions described in Table 1 may be prepared by mixing the non-ionic surfactant, aqueous phase (including orally acceptable solvents and water-soluble components), and water-insoluble compounds, using any conventional mixing technology.

For example, one method may comprise (i) preparing a flavor concentrate comprising surfactants, oil (including menthol, methyl salicylate, thymol, eucalyptol, or other flavor compounds) and a solvent; and (ii) diluting the flavor concentrate into an aqueous phase.

In another example, referring to Example 3, the method may comprise (i) preparing a flavor concentrate comprising a non-ionic surfactant comprising (i) a surfactant selected from the group consisting of polyol esters and sugar esters; a flavor component, such as, for example, oil (including menthol, methyl salicylate, thymol, eucalyptol, or other flavor compounds); and a solvent, and (ii) diluting the flavor concentrate into an aqueous phase comprising a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan.

Examples of flavor concentrates suitable for use according to embodiments described herein are disclosed in Table 3.

Methods

In some aspects, methods of use comprise contacting a subject's dental enamel surfaces and mucosa with the oral compositions described herein. The method of treatment may be by brushing with a dentifrice or rinsing with a dentifrice slurry or mouthwash. Other methods include contacting the topical oral gel, denture product, mouthspray, or other form with the subject's teeth and oral mucosa. The subject may be any person or animal whose oral cavity is contacted with the oral compositions. By animal is meant to include household pets or other domestic animals, or animals kept in captivity.

One aspect presented herein provides a method for treating plaque, gingivitis or gum disease in a subject in need thereof, comprising the step of applying to the tissues of the oral cavity of the subject, an amount of the composition according to the aspects presented herein effective to reduce symptoms associated with plaque, gingivitis or gum disease.

Table 1 below describes mouthwash compositions according to the aspects described herein.

TABLE 1

| Ingredients | Example A (% w/w) | Example B (% w/w) | Example C (% w/w) | Example D (% w/w) | Example E (% w/w) | Example F (% w/w) | Example G (% w/w) | Example H (% w/w) |
|---|---|---|---|---|---|---|---|---|
| Menthol | 0.048 | 0.048 | 0.048 | 0.048 | 0.048 | 0.048 | 0.048 | 0.048 |
| Methyl salicylate | 0.042 | 0.042 | 0.042 | 0.042 | 0.042 | 0.042 | 0.042 | 0.042 |
| Thymol | 0.059 | 0.059 | 0.059 | 0.059 | 0.059 | 0.059 | 0.059 | 0.059 |
| Eucalyptol | 0.089 | 0.089 | 0.089 | 0.089 | 0.089 | 0.089 | 0.089 | 0.089 |
| Flavor | 0.012 | 0.012 | 0.012 | 0.012 | 0.012 | 0.012 | 0.012 | 0.012 |
| Poloxamer 407[1] | 0.100 | 0.150 | 0.200 | 0.225 | 0.300 | 0.100 | 0.150 | 0.200 |
| Kolliphor® RH 40[2] | — | — | — | — | — | — | — | — |
| Sugar ester L-1695[3] | 0.100 | 0.150 | 0.200 | 0.075 | 0.100 | — | — | — |

TABLE 1-continued

| Ingredients | | | | | | | | |
|---|---|---|---|---|---|---|---|---|
| Habo Monoester P90[4] | — | — | — | — | — | 0.100 | 0.150 | 0.200 |
| Habo Monoester L90[5] | — | — | — | — | — | — | — | — |
| Sunsoft Q-12S[6] | — | — | — | — | — | — | — | — |
| Benzoic acid | 0.070 | 0.070 | 0.070 | 0.070 | 0.070 | 0.070 | 0.070 | 0.070 |
| Sodium benzoate | 0.080 | 0.080 | 0.080 | 0.080 | 0.080 | 0.080 | 0.080 | 0.080 |
| Sorbitol | 14 | 14 | 14 | 14 | 14 | 14 | 14 | 14 |
| Propylene glycol | 7 | 7 | 7 | 7 | 7 | 7 | 7 | 7 |
| Water | Q.S | Q.S | Q.S | Q.S | Q.S | Q.S | Q.S | Q.S |
| Total | 100 | 100 | 100 | 100 | 100 | 100 | 100 | 100 |
| Turbidity (NTU) | 12.51 | 3.49 | 2.37 | 10.61 | 4.09 | 12.17 | 6.84 | 2.78 |

| Ingredients | Example I (% w/w) | Example J (% w/w) | Example K (% w/w) | Example L (% w/w) | Example M (% w/w) | Example N (% w/w) | Example O (% w/w) | Example P (% w/w) |
|---|---|---|---|---|---|---|---|---|
| Menthol | 0.048 | 0.048 | 0.048 | 0.048 | 0.048 | 0.048 | 0.048 | 0.048 |
| Methyl salicylate | 0.042 | 0.042 | 0.042 | 0.042 | 0.042 | 0.042 | 0.042 | 0.042 |
| Thymol | 0.059 | 0.059 | 0.059 | 0.059 | 0.059 | 0.059 | 0.059 | 0.059 |
| Eucalyptol | 0.089 | 0.089 | 0.089 | 0.089 | 0.089 | 0.089 | 0.089 | 0.089 |
| Flavor | 0.012 | 0.012 | 0.012 | 0.012 | 0.012 | 0.012 | 0.012 | 0.012 |
| Poloxamer 407[1] | — | — | — | — | — | 0.050 | 0.075 | 0.100 |
| Kolliphor® RH 40[2] | 0.150 | 0.200 | 0.300 | 0.225 | 0.300 | — | — | — |
| Sugar ester L-1695[3] | 0.150 | 0.200 | 0.100 | — | — | — | — | — |
| Habo Monoester P90[4] | — | — | — | 0.075 | 0.100 | — | — | — |
| Habo Monoester L90[5] | — | — | — | — | — | 0.150 | 0.225 | 0.300 |
| Sunsoft Q-12S[6] | — | — | — | — | — | — | — | — |
| Benzoic acid | 0.070 | 0.070 | 0.070 | 0.070 | 0.070 | 0.070 | 0.070 | 0.070 |
| Sodium benzoate | 0.080 | 0.080 | 0.080 | 0.080 | 0.080 | 0.080 | 0.080 | 0.080 |
| Sorbitol | 14 | 14 | 14 | 14 | 14 | 14 | 14 | 14 |
| Propylene glycol | 7 | 7 | 7 | 7 | 7 | 7 | 7 | 7 |
| Water | Q.S | Q.S | Q.S | Q.S | Q.S | Q.S | Q.S | Q.S |
| Total | 100 | 100 | 100 | 100 | 100 | 100 | 100 | 100 |
| Turbidity (NTU) | 3.94 | 2.57 | 3.77 | 6.97 | 8.69 | 3.99 | 1.15 | 0.73 |

| Ingredients | Example Q (% w/w) | Example R (% w/w) | Example S (% w/w) | Example T (% w/w) | Example U (% w/w) | Example V (% w/w) | Example W (% w/w) | Example X (% w/w) |
|---|---|---|---|---|---|---|---|---|
| Menthol | 0.048 | 0.048 | 0.048 | 0.048 | 0.048 | 0.048 | 0.048 | 0.048 |
| Methyl salicylate | 0.042 | 0.042 | 0.042 | 0.042 | 0.042 | 0.042 | 0.042 | 0.042 |
| Thymol | 0.059 | 0.059 | 0.059 | 0.059 | 0.059 | 0.059 | 0.059 | 0.059 |
| Eucalyptol | 0.089 | 0.089 | 0.089 | 0.089 | 0.089 | 0.089 | 0.089 | 0.089 |
| Flavor | 0.012 | 0.012 | 0.012 | 0.012 | 0.012 | 0.012 | 0.012 | 0.012 |
| Poloxamer 407[1] | 0.100 | 0.150 | 0.200 | 0.225 | 0.300 | — | — | 0.075 |
| Kolliphor® RH 40[2] | — | — | — | — | — | 0.100 | 0.300 | — |
| Sugar ester L-1695[3] | — | — | — | — | — | — | — | — |
| Habo Monoester P90[4] | — | — | — | — | — | — | — | — |
| Habo Monoester L90[5] | 0.100 | 0.150 | 0.200 | 0.075 | 0.100 | 0.300 | 0.100 | — |

TABLE 1-continued

| Ingredients | Example Y (% w/w) | Example Z (% w/w) | Comparative Example CA (% w/w) | Comparative Example CB (% w/w) | Comparative Example CC (% w/w) | Comparative Example CD (% w/w) | Comparative Example CE (% w/w) | Comparative Example CF (% w/w) |
|---|---|---|---|---|---|---|---|---|
| Sunsoft Q-12S[6] | — | — | — | — | — | — | — | 0.225 |
| Benzoic acid | 0.070 | 0.070 | 0.070 | 0.070 | 0.070 | 0.070 | 0.070 | 0.070 |
| Sodium benzoate | 0.080 | 0.080 | 0.080 | 0.080 | 0.080 | 0.080 | 0.080 | 0.080 |
| Sorbitol | 14 | 14 | 14 | 14 | 14 | 14 | 14 | 14 |
| Propylene glycol | 7 | 7 | 7 | 7 | 7 | 7 | 7 | 7 |
| Water | Q.S | Q.S | Q.S | Q.S | Q.S | Q.S | Q.S | Q.S |
| Total | 100 | 100 | 100 | 100 | 100 | 100 | 100 | 100 |
| Turbidity (NTU) | 6.11 | 2.90 | 2.10 | 10.78 | 3.38 | 1.70 | 8.70 | 13.62 |

| Ingredients | Example Y (% w/w) | Example Z (% w/w) | Comparative Example CA (% w/w) | Comparative Example CB (% w/w) | Comparative Example CC (% w/w) | Comparative Example CD (% w/w) | Comparative Example CE (% w/w) | Comparative Example CF (% w/w) |
|---|---|---|---|---|---|---|---|---|
| Menthol | 0.048 | 0.048 | 0.048 | 0.048 | 0.048 | 0.048 | 0.048 | 0.048 |
| Methyl salicylate | 0.042 | 0.042 | 0.042 | 0.042 | 0.042 | 0.042 | 0.042 | 0.042 |
| Thymol | 0.059 | 0.059 | 0.059 | 0.059 | 0.059 | 0.059 | 0.059 | 0.059 |
| Eucalyptol | 0.089 | 0.089 | 0.089 | 0.089 | 0.089 | 0.089 | 0.089 | 0.089 |
| Flavor | 0.012 | 0.012 | 0.012 | 0.012 | 0.012 | 0.012 | 0.012 | 0.012 |
| Poloxamer 407[1] | 0.100 | 0.200 | 0.400 | — | — | — | — | — |
| Kolliphor ® RH 40[2] | — | — | — | 0.400 | — | — | — | — |
| Sugar ester L-1695[3] | — | — | — | — | 0.400 | — | — | — |
| Habo Monoester P90[4] | — | — | — | — | — | 0.400 | — | — |
| Habo Monoester L90[5] | — | — | — | — | — | — | 0.400 | — |
| Sunsoft Q-12S[6] | 0.300 | 0.200 | — | — | — | — | — | 0.400 |
| Benzoic acid | 0.070 | 0.070 | 0.070 | 0.070 | 0.070 | 0.070 | 0.070 | 0.070 |
| Sodium benzoate | 0.080 | 0.080 | 0.080 | 0.080 | 0.080 | 0.080 | 0.080 | 0.080 |
| Sorbitol | 14 | 14 | 14 | 14 | 14 | 14 | 14 | 14 |
| Propylene glycol | 7 | 7 | 7 | 7 | 7 | 7 | 7 | 7 |
| Water | Q.S | Q.S | Q.S | Q.S | Q.S | Q.S | Q.S | Q.S |
| Total | 100 | 100 | 100 | 100 | 100 | 100 | 100 | 100 |
| Turbidity (NTU) | 8.17 | 9.90 | 47.58 | 77 | 303 | 145 | 196 | 447 |

[1] Sigma aidrich.
[2] Cremophor ®RH 40, BASF.
[3] Sucrose laurate, Mitsubishi-Chemical Foods Corporation.
[4] Sucrose monopalmitate, Compass foods.
[5] Sucrose monolaurate, Compass foods.
[6] Monolauric acid decaglycerin ester, Taiyo Kagaku Co., Ltd.

The present invention is best illustrated but is not limited to the following examples.

EXAMPLES

Example 1: Solubility of the Bioactive Component of Compositions According to Some Aspects Presented Herein The turbidity of the compositions described in Table 1 was measured using a portable turbidity meter (Hanna instruments, Woonsocket, RI, HI93703). Table 1 reports the turbidity measured in Nephelometric Turbidity Units (NTU).

Referring to Table 1, the use of poly(oxyethylene)-poly(oxypropylene)-poly(oxyethylene) block copolymers alone resulted in non-transparent formulations (i.e., a NTU ranging from 20 to 100). In contrast, the use of a combination of a poly(oxyethylene)-poly(oxypropylene)-poly(oxyethylene) block copolymer, and a polyol ester resulted in transparent compositions (i.e., a NTU of less than 20, alternatively less than 10). These data suggest that the solubilization capacity for the bioactive component was greatly enhanced by combining the poly(oxyethylene)-poly(oxypropylene)-poly(oxyethylene) block copolymer with the surfactant comprising a polyol ester or sugar ester.

The ratio of the poly(oxyethylene)-poly(oxypropylene)-poly(oxyethylene) block copolymer to the surfactant comprising a polyol ester or sugar ester appeared to affect the observed turbidity of the oral care formulations. Referring to Example V, a ratio of the poly(oxyethylene)-poly(oxypropylene)-poly(oxyethylene) block copolymer to the surfactant comprising a polyol ester or sugar ester of 1:3 appeared optimal.

Example 2: Antimicrobial Efficacy of Compositions According to Some Aspects Presented Herein The antimicrobial efficacy of selected compositions described in Table 1 was evaluated. Populations of *Streptococcus mutans* were contacted with each formulation for 30 seconds. A commercially available alcohol-free mouthwash product (Listerine Zero®) was included as a positive control. Viable microorganisms were counted and data reported as a log reduction compared to negative control (deionized water) in Table 2.

TABLE 2

| Samples | Log reduction |
| --- | --- |
| Example A | >4.81 |
| Example B | >4.81 |
| Example C | >4.81 |
| Example D | >4.81 |
| Example E | 4.12 |
| Example F | >4.81 |
| Example G | >4.81 |
| Example H | 4.39 |
| Example I | >4.81 |
| Example K | 2.07 |
| Example L | 4.66 |
| Example N | >4.81 |
| Example Q | >4.81 |
| Example R | >4.81 |
| Example S | >4.81 |
| Example T | >4.81 |
| Example U | 4.36 |
| Example V | >4.81 |
| Example W | 3.99 |
| Example X | >4.81 |
| Example Y | >4.81 |
| Example Z | >4.81 |
| Positive control | >4.81 |
| Negative control | 0 |

Referring to Table 2, the antimicrobial efficacy of most compositions were comparable the positive control. Example E, H, K, L, W were less effective in inhibiting *S. mutans* compared to the positive control, which contain higher portions of Poloxamer 407 or Cremophor RH40, indicating the negative effect of Poloxamer 407 or Cremophor RH40 on the antimicrobial efficacy of bioactive oils. These data suggest that most of the oral care compositions presented herein have an antimicrobial efficacy similar to commercial alcohol-free mouthwashes.

Example 3: Preparation of Compositions According to Some Aspects Presented Herein Without intending to be limited to any particular theory, the compositions described in Table 1 may be prepared by mixing the non-ionic surfactant, aqueous phase (including orally acceptable solvents and water-soluble components), and water-insoluble compounds, using any conventional mixing technology.

For example, one method may comprise (i) preparing a flavor concentrate comprising surfactants, oil (including menthol, methyl salicylate, thymol, eucalyptol, or other flavor compounds) and a solvent; and (ii) diluting the flavor concentrate into an aqueous phase.

In another example, the method may comprise (i) preparing a flavor concentrate comprising a non-ionic surfactant comprising (i) a surfactant selected from the group consisting of polyol esters and sugar esters; a flavor component, such as, for example, oil (including menthol, methyl salicylate, thymol, eucalyptol, or other flavor compounds); and at least one orally acceptable solvent, and (ii) diluting the flavor concentrate into an aqueous phase comprising a surfactant selected from the group consisting of: poly(oxyethylene)-poly(oxypropylene)-poly(oxyethylene) block copolymers, poly(oxyethylene)-modified hydrogenated castor oils, and poly(oxyethylene)-modified fatty acid monoesters of sorbitan.

Examples of flavor concentrates suitable for use according to embodiments described herein are disclosed in Table 3.

TABLE 3

|  | Example a | Example b | Example c | Example d | Example e | Example f | Example g | Example h | Example i | Example j |
| --- | --- | --- | --- | --- | --- | --- | --- | --- | --- | --- |
| Menthol, methyl salicylate, thymol, eucalyptol and other flavor | 21.74 | 21.74 | 17.24 | 33.33 | 33.33 | 17.24 | 25.00 | 25.00 | 20.00 | 20.00 |
| Poloxamer 407[1] | 13.05 | 13.05 | 20.69 | 6.67 | 13.34 | 20.69 |  |  |  |  |
| Kolliphor® RH 40[2] |  |  |  |  |  |  | 22.50 | 15.00 | 24.00 | 8.00 |
| Sugar ester L-1695[3] |  | 13.05 | 6.90 |  |  |  |  | 15.00 | 8.00 |  |
| Habo Monoester P90[4] | 13.05 |  |  |  |  |  | 7.50 |  |  |  |
| Habo Monoester L90[5] |  |  |  | 20.00 | 13.33 | 6.90 |  |  |  | 24.00 |
| Propylene glycol | 39.13 | 39.13 | 41.38 | 40.00 | 40.00 | 41.38 | 45.00 | 45.00 | 48.00 | 48.00 |

TABLE 3-continued

| | | | | | | | | | | |
|---|---|---|---|---|---|---|---|---|---|---|
| Glycerol | | | | | | | | | | |
| Ethy lactate | | | | | | | | | | |
| Water | 13.03 | 13.03 | 13.79 | | | 13.79 | | | | |

[1] Sigma aldrich.
[2] Cremophor ®RH 40, BASF.
[3] Sucrose laurate, Mitsubishi-Chemical Foods Corporation.
[4] Sucrose monopalmitate, Compass foods.
[5] Sucrose monolaurate, Compass foods.

| | Example k | Example l | Example m | Example n | Example o | Example p | Example q | Example r | Example s | Example t | Example u |
|---|---|---|---|---|---|---|---|---|---|---|---|
| Menthol, methyl salicylate, thymol, eucalyptol and other flavor | 56.25 | 50.00 | 43.75 | 37.50 | 50.00 | 43.75 | 37.50 | 56.25 | 50.00 | 43.75 | 37.50 |
| Habo Monoester L90[1] | 33.75 | 30.00 | 26.25 | 22.50 | 30.00 | 26.25 | 22.50 | 33.75 | 30.00 | 26.25 | 22.50 |
| Propylene glycol | | | | | | | | 2.50 | 5.00 | 7.50 | 10.00 |
| Glycerol | | | | | 10.00 | 15.00 | 20.00 | | | | |
| Ethyl lactate | 10.00 | 20.00 | 30.00 | 40.00 | 10.00 | 15.00 | 20.00 | 7.50 | 15.00 | 22.50 | 30.00 |

[1] Sucrose monolaurate, Compass foods.

| | Example v | Example w | Example x | Example y | Example z | Example aa | Example ab | Example ac |
|---|---|---|---|---|---|---|---|---|
| Menthol, methyl salicylate, thymol, eucalyptol and other flavor | 56.25 | 50.00 | 43.75 | 37.50 | 35.71 | 35.71 | 30.00 | 30.00 |
| Habo Monoester L90[1] | 33.75 | 30.00 | 26.25 | 22.50 | 21.43 | 21.43 | 18.00 | 18.00 |
| Propylene glycol | 10.00 | 20.00 | 30.00 | 40.00 | 21.43 | 32.14 | 39.00 | 26.00 |
| Glycerol | | | | | 21.43 | 10.71 | 13.00 | 26.00 |

[1] Sucrose monolaurate, Compass foods.

| | Example ad | Example ae | Example af | Example ah | Example ai | Example aj | Example ak | Example al | Example am |
|---|---|---|---|---|---|---|---|---|---|
| Menthol, methyl salicylate, thymol, eucalyptol and other flavor | 50.00 | 43.75 | 37.50 | 50.00 | 43.75 | 37.50 | 50.00 | 43.75 | 37.50 |
| Habo Monoester L90[1] | 30.00 | 26.25 | 22.50 | 30.00 | 26.25 | 22.50 | 30.00 | 26.25 | 22.50 |
| Propylene glycol | 10.00 | 15.00 | 20.00 | 6.67 | 10.00 | 13.33 | 5.00 | 7.50 | 10.00 |
| Glycerol | 10.00 | 15.00 | 20.00 | 13.33 | 20.00 | 26.67 | 15.00 | 22.50 | 30.00 |

[1] Sucrose monolaurate, Compass foods.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A flavor concentrate comprising
   a) a flavor component comprising an oil;
   b) a non-ionic surfactant comprising (i) a poly(oxyethylene)-poly(oxypropylene)-poly(oxyethylene) block copolymer and (ii) a surfactant selected from the group consisting of polyol esters and sugar esters;
   c) at least one orally acceptable solvent;
   wherein the ratio of the poly(oxyethylene)-poly(oxypropylene)-poly(oxyethylene) block copolymer to the surfactant selected from the group consisting of polyol esters and sugar esters is from 1:10 to 10:1.

2. The flavor concentrate of claim 1, wherein the flavor component is in an amount from 17.24 to 33.33%.

3. The flavor concentrate of claim 1, wherein the oil comprises a bioactive component.

4. The flavor concentrate of claim 3, wherein the ratio of the non-ionic surfactant to the bioactive component is from 0.5 to 3.

5. The flavor concentrate of claim 3, wherein the bioactive component comprises an essential oil.

6. The flavor concentrate of claim 5, wherein the essential oil comprises menthol, methyl salicylate, thymol, eucalyptol, or a combination thereof.

7. The flavor concentrate of claim 1, wherein the poly(oxyethylene)-poly(oxypropylene)-poly(oxyethylene) block copolymer is a hydrophilic non-ionic surfactant comprising a triblock copolymer consisting of a central hydrophobic block of polypropylene glycol flanked by two hydrophilic blocks of polyethylene glycol (PEG).

8. The flavor concentrate of claim 1, wherein the poly(oxyethylene)-modified fatty acid monoester of sorbitan is polysorbate 80 or polysorbate 20.

9. The flavor concentrate of claim 1, wherein the sugar ester is selected from the group consisting of: sucrose laurate, sucrose monolaurate, sucrose palmitate, sucrose monopalmitate, and combinations thereof.

10. The flavor concentrate of claim 1, wherein the sugar ester is a sucrose ester or a fructose ester.

11. The flavor concentrate of claim 1, wherein the polyol ester is a glycerol ester.

12. The flavor concentrate of claim 1, wherein the polyol ester is monolauric acid decaglycerin ester.

13. The flavor concentrate of claim 1, wherein the orally acceptable solvent is selected from the group consisting of: water, polyol, sugar alcohols, a $C_{1-6}$ linear or branched alkyl lactate, triacetine, triethylcitrate, benzylic alcohol, and combinations thereof.

14. A method for preparing an oral care composition, the method comprising:
   (i) preparing the flavor concentrate according to claim 1; and
   (ii) diluting the flavor concentrate into an aqueous phase.

15. The method according to claim 14, wherein the oil comprises a bioactive component, and wherein the bioactive component is in an amount from 0.01 to 10 wt % of the oral care composition prepared.

16. A method for preparing an oral care composition, the method comprising:
   (i) preparing a flavor concentrate comprising
      a) a flavor component comprising an oil;
      b) a non-ionic surfactant comprising a surfactant selected from the group consisting of polyol esters and sugar esters;
      c) at least one orally acceptable solvent;
   (ii) diluting the flavor concentrate into an aqueous phase comprising a non-ionic surfactant comprising a poly(oxyethylene)-poly(oxypropylene)-poly(oxyethylene) block copolymer;
   wherein the ratio of the poly(oxyethylene)-poly(oxypropylene)-poly(oxyethylene) block copolymer to the surfactant selected from the group consisting of polyol esters and sugar esters is from 1:10 to 10:1.

17. The method according to claim 16, wherein the oil comprises a bioactive component, wherein the bioactive component is in an amount from 0.01 to 10 wt % of the oral care composition.

18. The method according to claim 17, wherein the bioactive component comprises an essential oil.

19. The method according to claim 18, wherein the essential oil comprises menthol, methyl salicylate, thymol, eucalyptol, or a combination thereof.

20. The method according to claim 17, wherein the ratio of the non-ionic surfactant to the bioactive component is from 0.5 to 3.

* * * * *